United States Patent
Stone

(10) Patent No.: US 9,804,133 B1
(45) Date of Patent: Oct. 31, 2017

(54) METHOD TO ENABLE THE USE OF LARGER INJECTION VOLUMES AND TO REDUCE EXTRA-COLUMN EFFECTS IN CHROMATOGRAPHIC SEPARATIONS

(71) Applicant: Mark A. Stone, San Rafael, CA (US)

(72) Inventor: Mark A. Stone, San Rafael, CA (US)

( * ) Notice: Subject to any disclaimer, the term of this patent is extended or adjusted under 35 U.S.C. 154(b) by 110 days.

(21) Appl. No.: 14/838,070

(22) Filed: Aug. 27, 2015

(51) Int. Cl.
*G01N 30/02* (2006.01)
*G01N 30/16* (2006.01)
*B01D 15/40* (2006.01)
*B01D 15/26* (2006.01)

(52) U.S. Cl.
CPC ........... *G01N 30/16* (2013.01); *B01D 15/265* (2013.01); *B01D 15/40* (2013.01); *G01N 2030/027* (2013.01)

(58) Field of Classification Search
CPC ...... G01N 30/16; G01N 30/46; G01N 30/461; G01N 30/462; G01N 30/463; G01N 2030/027; B01D 15/265; B01D 15/40
See application file for complete search history.

(56) References Cited

U.S. PATENT DOCUMENTS

| | | | | |
|---|---|---|---|---|
| 4,180,389 A | * | 12/1979 | Paul | B01D 15/12 95/11 |
| 4,554,071 A | * | 11/1985 | Ruijten | B01D 15/08 210/198.2 |
| 5,047,073 A | * | 9/1991 | Stetter | B01D 53/30 95/8 |
| 5,198,115 A | * | 3/1993 | Stalling | G01N 25/14 210/137 |
| 5,498,279 A | * | 3/1996 | Klemp | G01N 30/463 96/104 |
| 2007/0295664 A1 | * | 12/2007 | Glatz | G01N 30/462 210/656 |

OTHER PUBLICATIONS

Pesek et al., "Aqueous normal-phase chromatography using silica-hydride-based stationary phases", Trends in Analytical Chemistry, vol. 42, pp. 64-73, 2013.*

* cited by examiner

*Primary Examiner* — Natalie Huls
(74) *Attorney, Agent, or Firm* — Craig M. Stainbrook; Stainbrook & Stainbrook, LLP

(57) ABSTRACT

A method and apparatus for enabling larger injection volumes and for reducing extra column effects in chromatographic separations using focusing pre-columns placed upstream of the analytical, or preparative, column with applications in any chromatographic system where the requirement is that the focusing pre-column, placed upstream of the analytical column, allows larger injection volumes to be utilized and, by enabling efficient focusing of solutes onto the analytical column, results in a significant reduction of band broadening due to extra-column effects which act upstream of the analytical column.

15 Claims, 3 Drawing Sheets

METHOD TO ENABLE THE USE OF LARGER INJECTION VOLUMES AND TO REDUCE EXTRA-COLUMN EFFECTS IN CHROMATOGRAPHIC SEPARATIONS

CROSS REFERENCES TO RELATED APPLICATIONS

Not applicable.

STATEMENT REGARDING FEDERALLY SPONSORED RESEARCH OR DEVELOPMENT

Not applicable.

THE NAMES OR PARTIES TO A JOINT RESEARCH AGREEMENT

Not applicable.

INCORPORATION BY REFERENCE OF MATERIAL SUBMITTED ON A COMPACT DISC

Not applicable.

BACKGROUND OF THE INVENTION

Field of the Invention

The present invention relates generally to chromatography, and more particularly to high performance liquid chromatography or supercritical fluid chromatography systems, and still more particularly to a system and method for improving the sensitivity and, hence, the accuracy and precision of these techniques. It should be noted that methodology that is commonly referred to as supercritical fluid chromatography is, in some cases, done under conditions that are, in fact, subcritical. Therefore, it should be clarified that all references to supercritical fluid chromatography, in this patent application, are meant to also encompass subcritical fluid chromatography.

Background Discussion

Chromatographers often desire to obtain better sensitivity. A simple way to accomplish this is to increase the injection volume. However, the analyst has only a limited ability to do this as the chromatography will begin to degrade when larger volumes are injected. This is due to two phenomena: First, there is a distortion or "smearing" effect that occurs as the injection solvent (or diluent) begins to mix with the mobile phase solvent. This occurs because when two different solvents begin to mix (even when the solvents are completely miscible with one another) they do not dissolve into one another immediately. As a result, some distortion and spreading of the injected sample occurs. Second, as an increasingly larger volume is injected, there is some degree of band broadening due directly to the volume of the injection itself.

In some cases, the use of larger injection volumes may be possible simply by using an injection solvent that is chromatographically weaker than the mobile phase (predominantly aqueous in the case of reversed phase liquid chromatography). Assuming the method parameters are such as to enable efficient focusing, this would allow for larger injection volumes, despite the issues described above, inasmuch as the solute (or analyte) peaks would be focused into sharper bands at the head of the analytical column. However, this option is only available in situations where the solutes have sufficient solubility, and where the sample matrix is sufficiently dissolved or dispersed, in these chromatographically weak injection solvents. In the majority of cases this is not possible, and injection solvents chromatographically stronger than the mobile phase must be used. The use of these stronger injection solvents results in the mobile phase being transiently stronger during the time when the injected sample is being transferred onto the column and, therefore, very inefficient focusing occurs at the head of the column.

Therefore, other than in those limited cases where chromatographically weak injection solvents can be used, a different approach must be found to increase the injection volume. The approaches reported in the literature have generally made use of column switching techniques. These systems often use a two-part process: in the first step a large volume is injected and concentrated onto a trap, and in the second step a switching valve is opened or switched and the solutes are transferred from the trap onto the analytical column. This technique has also been used with a membrane, and a solid-phase-microextraction fiber as the trap. Because of the complex nature of these processes, these approaches can be harder to run and more difficult in terms of troubleshooting and training. In addition, these types of setups are undesirable in pharmaceutical GMP environments, as the additional hardware must be formally qualified. Finally, these approaches can be problematic in terms of the additional dead volume contributed by the extra hardware that is needed.

BRIEF SUMMARY OF THE INVENTION

The present invention is a system and method for increasing the injection volume, and thereby increasing the sensitivity and, hence, the accuracy and precision, of liquid chromatography or supercritical fluid chromatography techniques. The method involves the use of a focusing pre-column placed prior to the analytical column and connected to the analytical column with a fluid line. No valve or additional hardware is required. The purpose of the pre-column is two-fold: First it serves to separate the injection solvent from the solutes by allowing the injection solvent to move through more quickly, so that when the solutes reach the analytical column, they focus at the head of the column in a far more effective manner given that the injection solvent is "out of the way". Second, it further enables efficient focusing of the solutes onto the head of the analytical column by virtue of a design wherein the linear velocity of the solutes on the focusing pre-column is greater than is the linear velocity of the solutes on the analytical column. This differential in linear velocity is critical for efficient focusing.

The invention may apply to any chromatographic system where the requirement is that a focusing pre-column, placed upstream of the analytical column, allows larger injection volumes to be utilized, including but not limited to conditions in which the injection solvent is chromatographically stronger than the initial mobile phase composition (which represents the majority of applications). In some cases, the present invention allows large injection volumes of solvents that are not miscible with the mobile phase. Additionally, this approach results in a significant reduction of band broadening due to the extra-column effects that act upstream of the analytical column. This is accomplished as the pre-column enables efficient focusing of the solutes onto the head of the analytical column. In the case of reversed phase liquid chromatography this may be accomplished, for example, if the analytical column contains an octadecylsilane stationary phase (commonly referred to as C18), and the pre-column contains a cyano stationary phase. The cyano phase allows the injection solvent to be separated from the solutes, as the former is less retained than the latter. Subsequently, due to the fact that the cyano phase is less retentive than the C18 phase, efficient focusing onto the head of the analytical column is enabled as the linear velocity of the solutes will be higher on the pre-column than on the analytical column.

If the focusing pre-column is made with silica hydride material it would in particular enable large injection volumes of polar solutes when using a non-polar injection solvent. This occurs as silica hydride is known to retain polar solutes in the presence of a relatively non-polar solvent by what is known as the Aqueous Normal Phase mechanism.

If this approach is used in the supercritical fluid, classical normal phase, or in the hydrophilic interaction liquid chromatography (HILIC) modes, the same approach described above may be employed, i.e., with the focusing pre-column containing a less retentive stationary phase than the analytical column. Alternatively, another approach that may be effective in these cases is to use a pre-column containing C18 or another relatively non-polar phase. This approach may be especially beneficial if the injection solvent is aqueous or largely aqueous; in that circumstance, the solutes will be well retained on the focusing pre-column in the presence of the aqueous injection solvent, but will be efficiently transferred and focused onto the head of the analytical column as soon as the injection solvent is out of the way and the mobile phase begins to move through.

It is desirable to have the focusing pre-column also serve as a guard column. In order to accomplish this, components that would strongly (or irreversibly) sorb onto the analytical column must also strongly (or irreversibly) sorb onto the pre-column. In order to encourage this sorption to occur on the pre-column, some portion of the pre-column can be made with a more retaining or more sorptive stationary phase, including even the same stationary phase as is used in the analytical column.

Focusing pre-columns may also be used for preparative separations. A common problem in preparative separations is transient desolubilizing of solutes after injection. This is especially common when using the supercritical fluid mode, where the sample, which is dissolved in a liquid solvent, is injected into a mobile phase that is predominantly supercritical or subcritical. The use of the focusing pre-column for preparative separations, in addition to having all the benefits described above, would also allow the solutes to re-dissolve into the mobile phase before being transferred and focused onto the head of the analytical column.

Those skilled in the art will appreciate that the conception upon which this disclosure is based may readily be used as a basis for designing other structures, methods, and systems for carrying out the several purposes of the present invention. It is important, therefore, that the claims are regarded as including such equivalent compositions, constructions, and methods as far as they do not depart from the spirit and scope of the present invention. Rather, the fundamental aspects of the invention, along with the various features, structures, compositions, and method steps that characterize the invention, are pointed out with particularity in the claims annexed to and forming a part of this disclosure. For a better understanding of the present invention, its advantages and the specific objects attained by its uses, reference should be made to the accompanying drawings and descriptive matter in which there are illustrated the preferred embodiments.

BRIEF DESCRIPTION OF SEVERAL VIEWS OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

Figure 1:
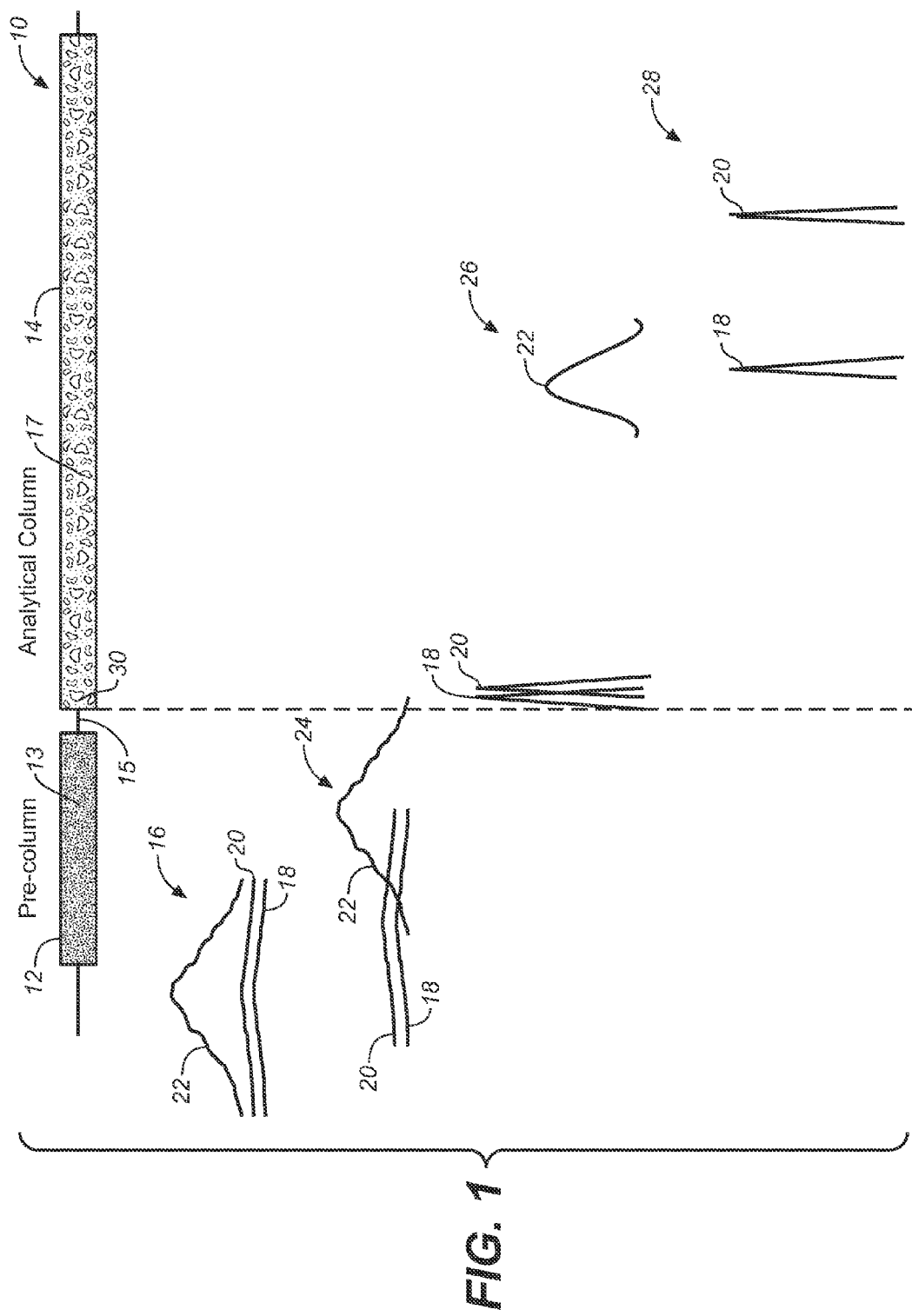
FIG. 1 is a highly schematic illustration showing the effect of a focusing pre-column in separating an injection solvent from solutes, such that the solutes can then focus at the head of the analytical column.

Referring first to FIG. 1, there is schematically illustrated therein a chromatography column apparatus 10 comprising a focusing pre-column 12 (hereinafter referred to simply as a pre-column) and an analytical column 14. In each of the several embodiments of this invention, the properties of the focusing pre-column are such as to accomplish separation of the solutes from the injection solvent and, subsequently, enable efficient focusing of the solutes onto the head of the analytical column. FIG. 1 presents an example of how this process may occur by depicting several snapshots in time of an analytical separation. In the first snapshot 16, two solutes, 18, 20, represented by the small peaks in the top left portion of the figure, are being injected in a volume of injection solvent 22, represented by the large peak in the top left portion of the figure.

Three subsequent snapshots in time are then represented (read from top to bottom), 24, 26, 28. Since the injection solvent 22 is minimally retained on the pre-column, it moves through quickly (see second snapshot 24). And the solutes, 18, 20, which are more retained on the pre-column, move through more slowly. As a result, by the time the solutes reach the analytical column (see third snapshot, 26), the injection solvent 22 is "out of the way," and the solutes can therefore effectively focus at the head 30 of the analytical column 14. Lastly, as the method proceeds the solutes can then separate as sharp peaks (see fourth snapshot, 28). For the focusing process to be efficient, the design of the focusing pre-column must be such that the linear velocity of the solutes on the pre-column is greater than the linear velocity of the solutes on the analytical column during transfer from the former to the latter.

By efficiently focusing solutes at the head 30 of the analytical column 14, including, but not limited to those cases in which the injection solvent is chromatographically stronger than the initial mobile phase composition (which represents the majority of situations), the system and apparatus described above enables larger volumes of such solvents to be injected. It also has the potential to reduce, or (in the best cases) cancel out entirely, all of the extra column effects that act upstream of the analytical column. This includes band broadening due to the volume and time of the injection, band broadening due to the length and diameter of the connecting tubing between the injection system and the column, and band broadening due to dead volume in the fittings upstream of the column.

In addition, if the pre-column 12 is also used as the guard column, any band broadening due to voids or insufficient packing of the guard column (a common problem in chromatography) will be cancelled as well. These band broadening phenomena have been discussed extensively in the literature and mathematical relationships have been developed. For example, it has been shown that the maximum volume that can be injected on a chromatographic system ($V_i$) is proportional to ($\alpha$) the column's internal diameter ($d_c$) squared, and to the square root of the column's length and the particle diameter (given by L and $d_p$, respectively). Similar relationships exist for the other extra column effects.

$$V_i \alpha d_c^2 (L d_p)^{1/2}$$

It is clear that these extra column effects are strongly dependent on the internal diameter of the column. Therefore, these issues are especially important with methods that make use of smaller diameter columns in order to improve sensitivity or to minimize solvent consumption and waste generation, or in Ultra-High Pressure Liquid Chromatography where smaller diameter columns are typically used to minimize the extent to which radial temperature gradients develop in the column.

It is an object and advantage of the present invention to overcome the shortcomings in existing chromatography techniques and to achieve a superior approach.

A preferred embodiment of the present invention can be visualized by referring, again, to FIG. 1, wherein a pre-column 12 is placed upstream of the analytical column 14 and coupled to the analytical column with a fluid line 15. In this embodiment, the pre-column 12 contains a stationary phase 13 that is less retentive than the stationary phase 17 of the analytical column. In the case of reversed phase liquid chromatography, this may be accomplished, for example, if the analytical column contains an octadecylsilane (subsequently referred to as C18), or other non-polar, stationary phase; and the pre-column contains a cyano, or other fairly polar, stationary phase. For both the pre-column and the analytical column, the chromatographic particles may be composed of conventional silica, polymeric material, or other suitable material. As the injected sample moves through the pre-column, the solutes are more retained on the pre-column than is the injection solvent and, therefore, the injection solvent moves through the pre-column and onto the analytical column more quickly than the solutes (as is shown in FIG. 1). Therefore, by the time the solutes are transferred onto the analytical column (see third snapshot, 26, in FIG. 1) the injection solvent is no longer present and cannot interfere with the focusing of the solutes at the head of the analytical column. Furthermore, the fact that the pre-column is composed of a less retentive phase than the analytical column enables efficient focusing onto the head of the analytical column as the linear velocity of the solutes will be higher on the pre-column than on the analytical column, and this differential in linear velocity is necessary for efficient focusing. The entire process is depicted in FIG. 1 above.

It has been observed that optimal results will often be achieved if the system were designed in such a way as to accomplish mixing of the injected sample with the mobile phase prior to it reaching the focusing pre-column. This may be accomplished simply by placing longer and/or larger internal diameter tubing, or fittings containing dead volume, or even a small empty column or cartridge, upstream of the pre-column. But is more effectively accomplished by installing a mixer upstream of the pre-column. Radial mixers should provide some benefit, however, longitudinal mixers, and especially dynamic mixers, which accomplish longitudinal mixing with the least amount of spreading of the injected components, may offer the best results.

An alternative embodiment of the invention can be described as being equivalent to the system and apparatus described above, but the pre-column may be composed of silica hydride particles. This variation is applicable when doing reversed phase chromatography and where at least some of the solutes are polar, and is primarily beneficial when the injection solvent is entirely or predominantly organic (non-aqueous). The benefit of this arrangement is that silica hydride material is known to be effective at retaining polar solutes in the presence of a non-polar solvent. This is accomplished by what is referred to as an Aqueous Normal Phase mechanism. In this embodiment it may be beneficial to minimize the mixing of the injected sample with the mobile phase prior to reaching the pre-column, as the most efficient focusing of the polar solutes by the Aqueous Normal Phase mechanism will occur in the presence of "pure" organic solvent. There are several factors that may be considered to minimize mixing. One is to minimize the length and the internal diameter of the connecting tubing upstream of the focusing pre-column. In fact, it may be beneficial to place the focusing pre-column immediately downstream of the point of injection, or at least as close as possible. The analytical column may be placed directly following, or may be placed in its usual location (perhaps in the HPLC oven chamber) with a length of tubing connecting the pre-column and the analytical column. Another option is to use a timed injection approach, as this delivers the injected sample onto the column with minimal mixing into the mobile phase.

Another embodiment may comprise a combination of the two preceding, wherein the pre-column is composed of silica hydride material, but with a fairly polar phase such as cyano bonded to it. When used in the reversed phase mode, a pre-column of this type would have the ability to separate both polar and non-polar solutes from the injection solvent, and enable efficient focusing of these solutes on the head of the analytical column, by virtue of both of the mechanisms described above.

Figure 2:
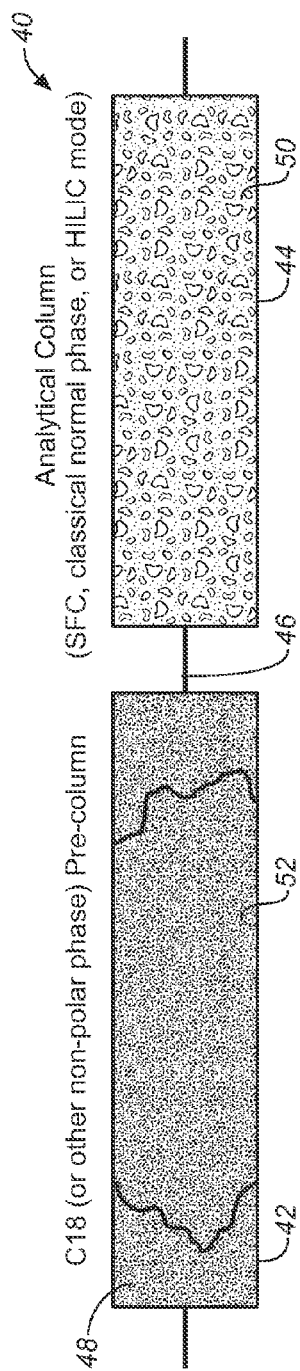
FIG. 2 is a highly schematic illustration showing one embodiment of the invention, which may be used for supercritical fluid, classical normal phase, or HILIC modes of separation.

If the inventive system is employed when conducting separations in the supercritical fluid (SFC), classical normal phase, or in the hydrophilic interaction liquid chromatography (HILIC) mode, the same approach described above may be used, i.e., the focusing pre-column will contain a less retentive stationary phase than the analytical column. Alternatively, however, in still another embodiment use may be made of a pre-column that contains a C18, or other fairly non-polar phase. This approach is especially beneficial if the injection solvent were aqueous or largely aqueous as, in that circumstance, the solutes would be well retained on the focusing pre-column in the presence of the aqueous injection solvent, but would be efficiently transferred and focused onto the head of the analytical column as soon as the injection solvent were out of the way and the predominantly organic mobile phase began to move through. FIG. 2 presents a schematic depiction of how this approach works. The figure (in the pre-column portion 42) depicts the plug 52 of injected sample moving through the pre-column 42. The solutes will be retained on the pre-column, by a reversed phase mechanism, given that the pre-column contains a non-polar stationary phase, and given that the solutes are in a predominantly aqueous solvent.

Once the diluent moves through and the supercritical, classical normal phase, or HILIC mobile phase begins to take over, it is expected, due to the predominantly organic nature of these mobile phases, that these solutes would be efficiently eluted from the non-polar pre-column and then re-focused at the head of the polar analytical column. This occurs due to the fact that the organic mobile phase is chromatographically strong in the reversed phase mode (i.e. on the pre-column) but chromatographically weak in the supercritical, classical normal phase, or HILIC modes (i.e. on the analytical column). A key observation with respect to this approach is that it would be preferable to minimize mixing of the injection solvent into the mobile phase. If mixing is minimized the solutes would be present primarily in diluent, during passage through the focusing pre-column, and therefore would be most effectively retained on the pre-column (especially if the diluent were entirely, or predominantly, aqueous). This may be accomplished by the recommendations previously given. In addition, it may also be beneficial, in some cases, to have salt present in the sample as this would slow the rate of mixing of the sample (which is fairly polar in this embodiment) into the mobile phase (which would be less polar in this embodiment).

Another version of this approach with respect to supercritical fluid, classical normal phase, or HILIC modes, may be a combination of the two approaches described above, i.e. a phase which is predominantly non-polar but which does possess a moderate amount of polarity causing it to exhibit a small degree of retention in the mode of separation being used, but less than the analytical column. For example, a column which contains hydrophobic chains with hydroxyl groups on the end.

With respect to all of the embodiments, variations, and system designs described above, it may be desirable to have the focusing pre-column also serve as a guard column. In order to accomplish this, components which would strongly (or irreversibly) sorb onto the analytical column must also strongly (or irreversibly) sorb onto the pre-column. And this may not happen with some of the approaches described above as the pre-column will often be made of a less sorptive material.

Figure 3:
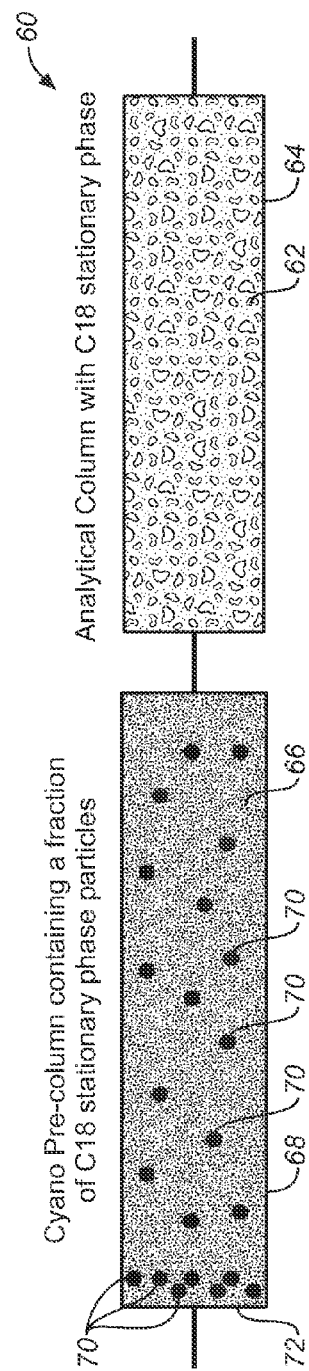
FIG. 3, is a highly schematic illustration showing another embodiment of the present invention, wherein the focusing pre-column is designed to additionally function as a guard column.

As depicted in FIG. 3 this sorption can be encouraged to occur on the pre-column, in another preferred embodiment of the inventive system 60, if some portion of the pre-column is made with a more retaining or more sorptive material, perhaps even the same stationary phase as is used in the analytical column. In the example depicted in FIG. 3, a C18 stationary phase 62 is used as the analytical column 64 and the less retentive cyano phase 66 is used, primarily, in the pre-column 68. However, some fraction of the particles packed into the pre-column are made with C18 stationary phase (represented by the dark circles 70 in the figure). In this way, it should be possible to get the benefits of a focusing pre-column and, in addition, the pre-column would also act as a guard column and, therefore, protect the analytical column.

The embodiment shown in FIG. 3 shows the C18 particles concentrated at the head 72 of the pre-column 68 and then dispersed in a less concentrated fashion throughout the rest of the pre-column. However, this is just one manifestation and others may be used.

Figure 4:
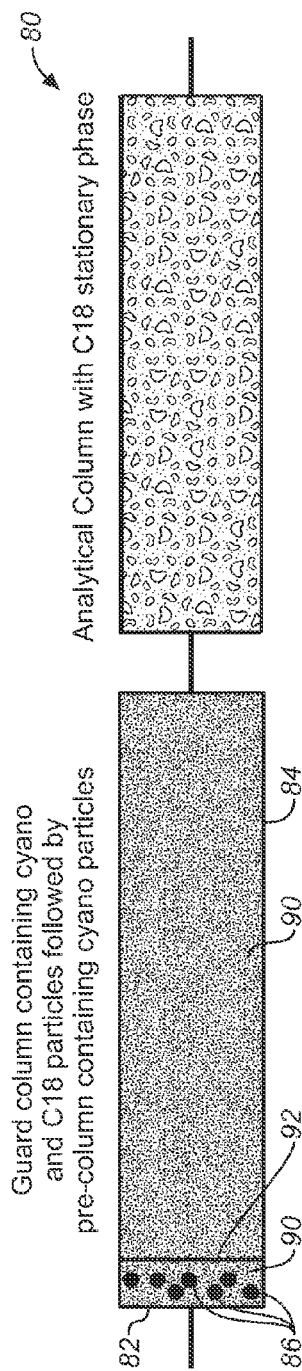
FIG. 4 is also a highly schematic illustration showing still another preferred embodiment of the present invention, wherein the guard column is separated from the focusing pre-column, and the guard column is composed of a combination of cyano and C18 material and the pre-column is composed of cyano material

Looking next at FIG. 4, in still a further preferred embodiment 80 the guard column and the pre-column form two distinct parts 82, 84. Following from the example above, the guard column 82 could be a short segment upstream of the pre-column composed partly of cyano or other fairly polar, material, and partly of C18, or other fairly non-polar, material 86; and the pre-column 84 which may be made entirely with cyano 90, or other fairly polar, material would follow. The partition or separation 92 between the guard column 82 and the pre-column 84 is represented by the vertical line. In this way, any components that would tend to sorb onto the analytical column will sorb onto the guard column. Sorption to the guard column could be further promoted if the underlying particle was more sorptive in nature. For example, if type A silica were used in the guard column and type B silica were used in the pre-column and the analytical column. These designs allow the guard column to serve its purpose of keeping the analytical column clean. Furthermore, with this design, the guard column, which needs more frequent replacement, is small and relatively inexpensive. Alternatively, the guard column could be of a composition identical to that of the analytical column. However, in this circumstance, somewhat less efficient focusing may be observed as broadening of the chromatographic peaks would occur during transfer from the guard column to the pre-column. It is for this reason that the design above is preferred.

Figure 5:
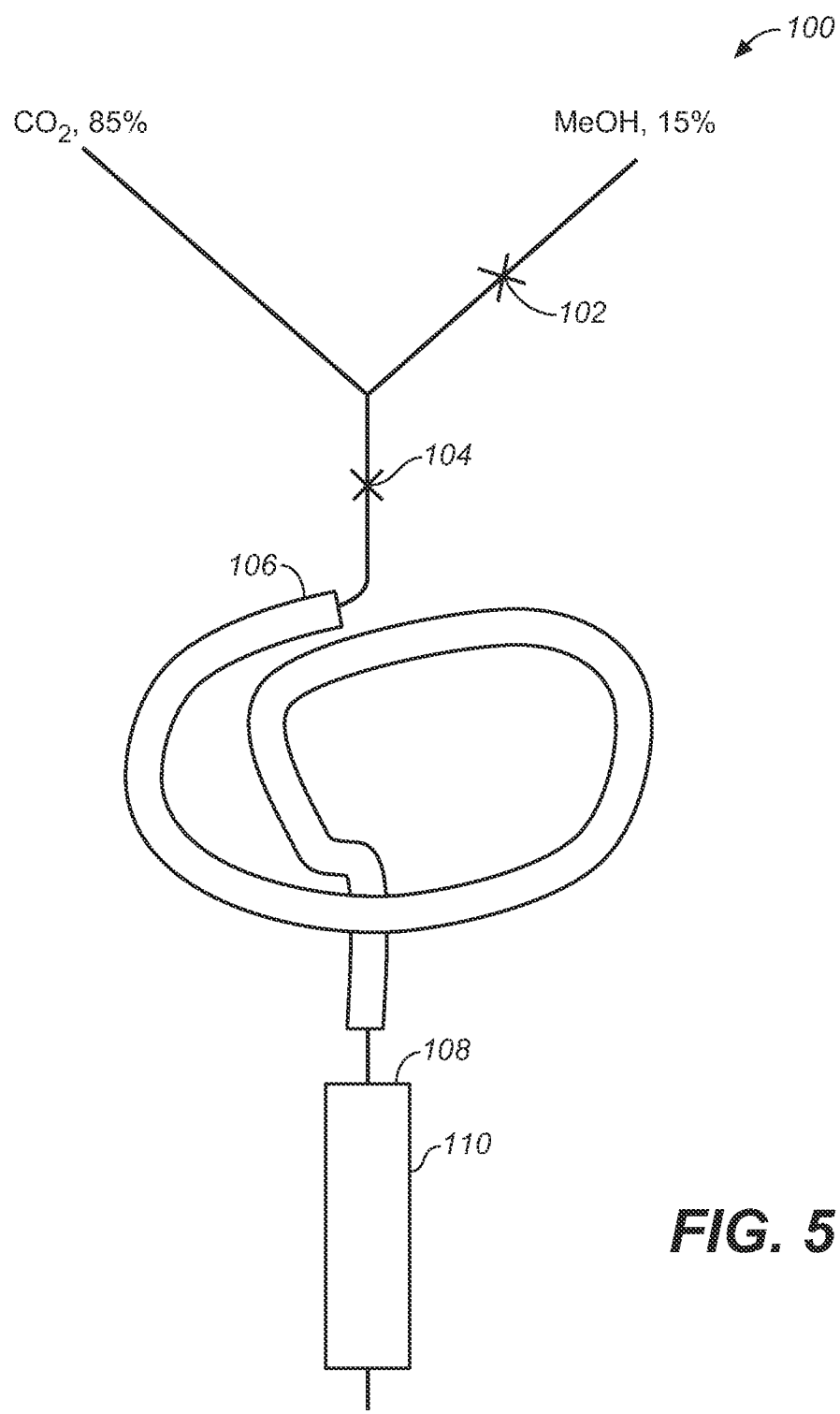
FIG. 5 is a highly schematic illustration showing another, alternative, embodiment of the present invention, wherein the focusing pre-column is used for preparative supercritical fluid chromatography.

Focusing pre-columns may also be used for preparative separations, as illustrated in the preferred embodiment 100 of the present invention, as shown in FIG. 5. In preparative separations the goal is generally to collect as much sample as possible. Therefore, the analyst usually injects a fairly large quantity (and often volume) of sample at a selected injection point or points 102, 104. As a result, a phenomenon is often observed, whereby the injected solutes may transiently desolubilize following injection. This is especially common when using the supercritical fluid mode, where the sample, which is dissolved in a liquid solvent, is introduced into a mobile phase that is predominantly supercritical or subcritical. In this embodiment, the use of the focusing pre-column 106, in addition to having all the benefits described previously, also provides time and space for the solutes to re-dissolve into the mobile phase before being transferred and focused onto the head 108 of the analytical column 110. With this approach the two preferred options 102, 104, where the sample can be injected, are shown by the Xs in FIG. 5. It should be noted that transient desolubilization, described above for supercritical fluid separations, can also occur for other modes of separation, as well as for separations conducted on an analytical scale. In all cases, the embodiment described here should minimize this problem.

In all of the embodiments and variations discussed above, the design is such that the linear velocity of the solutes is higher on the pre-column than on the analytical column, during transfer from the former to the latter. In all of these embodiments it may additionally be beneficial for the internal cross-sectional dimension of the focusing pre-column to be narrower than that of the analytical, or preparative, column. This will further increase the linear velocity of the solutes on the focusing pre-column as compared to the analytical column, and thereby contribute to even more efficient focusing at the head of the analytical, or preparative, column.

In all of the embodiments discussed above, in cases where the analytical column is maintained at an elevated temperature, the focusing pre-column may be used to deliver the mobile phase, which is initially at a lower temperature, to the column, which is located in a heated zone and is at an elevated temperature. If used in this manner the focusing pre-column assembly may be located partly outside of and partly inside of the heated zone. In this way the mobile phase is heated as it passes through the focusing pre-column. There is generally band broadening that occurs when a mobile phase moves through a column with non-uniform temperature zones. However, in any of the embodiments of the present invention, the system is designed to have efficient re-focusing of the solute peaks at the head of the analytical column, and this cancels out any such band broadening. It is necessary, however, for the mobile phase to reach the temperature of the analytical column prior to entering the analytical column. Alternatively, a design could be utilized wherein the pre-column is entirely outside of, or entirely inside of, the heated zone.

The various embodiments described above may also be used to enable more efficient, and more easily executed, multidimensional chromatography. One of the difficulties encountered in multidimensional chromatography is that analysts are limited to methodologies where the different stages of the separation utilize mobile phases that are compatible with one another. The techniques described above would provide a solution to this problem. In the same way that they allow injection of solvents typically less desirable for a given mode of separation, they likewise allow less desirable solvents to be delivered from one stage to the next stage of a multidimensional separation.

In some cases, it may be beneficial to utilize focusing pre-columns in two stages. For example, if running reversed phase chromatography, a pre-column with a cyano phase may be followed by a pre-column with a phenyl phase which, in turn, is followed by an analytical column composed of a hydrophobic phase such as C18 or graphite. In this case, focusing will occur on the head of the phenyl column and a second focusing event will occur at the head of the analytical column. Systems could also be setup that utilize more than two focusing stages.

One notable application that those of ordinary skill in the art will recognize is the use of focusing pre-columns in combination with TurboFlow columns for the analysis of samples wherein it is desired to analyze small molecules, but where large molecules are present as an interference such that it is beneficial to remove them. TurboFlow columns, which are commercially available, are designed to let large molecules such as proteins move through more quickly than small molecules. This is accomplished by virtue of the fact that these columns generate turbulent flow conditions and, hence, leverage the difference in diffusion rates of large molecules and small molecules. Systems are generally designed with a valve to divert the early eluting large molecules to waste. The valve is subsequently switched and the separation of the small molecules proceeds. The complication arises in that the small molecules elute from the TurboFlow column with poor peak shapes and, therefore, must be efficiently focused onto the head of the analytical column. In order to accomplish this, a setup is typically utilized wherein another fluid line, which delivers a chromatographically weak solvent, is teed in to the primary analytical line, in order to render the resulting (combined) mobile phase as chromatographically weak and thereby allow efficient focusing. However, this results in a fairly complex system with additional valving, and the associated software which is required to control said valving. The use of a focusing pre-column placed between the TurboFlow column and the analytical column would offer a more simple way to enable efficient focusing at the head of the analytical column, without requiring the use of additional hardware and software.

The use of focusing pre-columns would also be beneficial in situations where a solute undergoes a reaction or conversion after being injected into the mobile phase. This might include acid/base reactions, complexations, or conversions from one isomeric form to another. When such conversions occur while the solute is traveling through the analytical column, the result is broad and skewed chromatographic peaks due to the fact that the solute exists in two different forms as it is moving through the column. If, however, a pre-column is used, in any of the variations described above, the pre-column would allow time for the reaction or conversion to occur and then enable efficient focusing of the solute onto the head of the analytical column, thus providing a solution to this problem. It would be necessary, for this application, that the method to be designed such that the solute spends a sufficient period of time on the pre-column for the reaction or conversion to take place.

The following data were generated using the embodiment of the invention described above. A series of injections were first made using a Phenomenex Gemini C18 column (with dimensions of 4.6×150 mm, 5 μm) as the analytical column, with no focusing pre-column being used. Mobile phase A was 95/5 water/acetonitrile with 0.1% (v/v) formic acid and mobile phase B was 95/5 acetonitrile/water with 0.12% (v/v) formic acid. The gradient began with a 7 minute isocratic hold at 5% B, then increased linearly to 80% B at 35 minutes, and then to 95% B at 37 minutes. The composition was held at 95% B for three minutes, and the system was then re-equilibrated to 5% B over an interval of 12 minutes. The flow rate was 0.8 mL/minute. The maximum injection volume was defined as the point at which the two most closely eluting peaks "just begin to lose baseline resolution". A series of injection volumes were tried until the maximum injection volume (using this definition) was reached. The same experiment was then repeated with a cyano column (4.6×100 mm, 10 μm) placed upstream of the analytical column as a focusing pre-column.

The maximum injection volumes that were possible with no focusing pre-column were as follows:

Acetonitrile, 30 uL
Methanol, 40 uL
DMSO, 40 uL
90/10 Methanol/Water, 50 uL
80/20 Methanol/Water, 100 uL The maximum injection volumes that were possible with the focusing pre-column in place were as follows:

Acetonitrile, 200 uL
Methanol, 140 uL
DMSO, 200 uL
90/10 Methanol/Water, 140 uL
80/20 Methanol/Water, 160 uL This provides a rudimentary proof of concept that larger injection volumes were made possible by use of the approach described in this patent.

While the foregoing describe and illustrate only some exemplary embodiments of the present invention, it is to be understood that the present invention covers all variations, modifications and changes thereof which will occur to those persons skilled in the art and to other persons after having been exposed to the present patent application. Therefore, the above description and illustrations should not be construed as limiting the scope of the invention, which is defined by the appended claims.

What is claimed as invention is:

1. A column chromatography apparatus enabling larger injection volumes and minimizing extra column effects acting upstream of the column, comprising:
   an analytical column having a stationary phase with a head;
   a focusing pre-column in fluid communication with said analytical column and placed upstream of said analytical column, wherein said focusing pre-column includes a stationary phase which separates solutes from the molecules of an injection solvent and enables focusing of solutes onto said head of said analytical column;
   wherein said stationary phase of said focusing pre-column separates solutes from the molecules of injection solvent to focus the solutes onto the head of the analytical column, and wherein a portion of said stationary phase of said focusing pre-column contains sorptive materials thereby enabling said focusing pre-column to additionally function as a guard column.

2. The column chromatography apparatus of claim 1, further including a separate guard column portion having a stationary phase and a pre-column portion having a stationary phase.

3. The column chromatography apparatus of claim 2, wherein said guard column portion is upstream of said pre-column portion.

4. The column chromatography apparatus of claim 3, wherein said guard column portion includes a retentive stationary phase enabling it to sorb material that would be sorbed by said analytical column, and wherein said guard column portion is still less retentive than said stationary phase of said analytical column, and further wherein said stationary phase of said pre-column portion is less retentive than both said stationary phase of said guard column portion and said stationary phase of said analytical column.

5. The column chromatography apparatus of claim 3, wherein said guard column portion is of identical composition to said analytical column.

6. The column chromatography apparatus of claim 5, and wherein said stationary phase of said pre-column portion is less retentive than both said stationary phase of said guard column portion and said stationary phase of said analytical column.

7. The column chromatography apparatus of claim 1, wherein when used in the reversed phase mode said stationary phase of said focusing pre-column comprises particles of silica hydride to retain polar solutes in the presence of a non-polar solvent.

8. The column chromatography apparatus of claim 7, wherein the length and the internal diameter of connecting tubing upstream of said focusing pre-column are sized to minimize mixing of an injected sample with a mobile phase prior to reaching the focusing pre-column.

9. A column chromatography apparatus enabling larger injection volumes and minimizing extra column effects acting upstream of a column, comprising:
   an analytical column having a stationary phase with a head;
   a focusing pre-column in fluid communication with said analytical column and placed upstream of said analytical column, wherein said focusing pre-column includes a stationary phase which separates solutes from the molecules of an injection solvent and enables focusing of solutes onto said head of said analytical column;
   wherein when used in a reversed phase mode said stationary phase of said focusing pre-column comprises particles of silica hydride to retain polar solutes in the presence of a non-polar solvent; and
   wherein said stationary phase of said focusing pre-column comprises silica hydride particles with a generally polar phase bonded to said silica hydride particles, thereby enabling said focusing pre-column to retain non-polar solutes.

10. The column chromatography apparatus of claim 9, wherein when used in the supercritical fluid, classical normal phase, or hydrophilic interaction liquid chromatography modes, said stationary phase of said focusing pre-column comprises particles of non-polar material effective at retaining solutes when the injection solvent is aqueous or predominantly aqueous thereby allowing an injection solvent to move through said pre-column more quickly than the solutes.

11. The column chromatography apparatus of claim 9, wherein said focusing pre-column length and the internal diameter of connecting tubing upstream of said focusing pre-column are sized to minimize mixing of an injected sample with a mobile phase prior to reaching the focusing pre-column.

12. The column chromatography apparatus of claim 9, wherein said stationary phase of said focusing pre-column comprises predominantly non-polar material with a degree of polarity thereby causing it to exhibit a degree of retention for the mode of separation being used, but wherein the retention is less than the retention of said stationary phase of said analytical column.

13. The column chromatography apparatus of claim 9, wherein said stationary phase of said focusing pre-column is less retentive than said stationary phase of said analytical column, thereby allowing an injection solvent to move more quickly than solutes through said focusing pre-column, and furthermore where the linear velocity of the solutes will be higher on said focusing pre-column than on said analytical column because the former is less retentive than the latter and thereby enabling focusing of the solutes at said head of said analytical column.

14. The column chromatography apparatus of claim 9, further including mixing apparatus to facilitate mixing of an injected sample with a mobile phase prior to its reaching said focusing pre-column.

15. A column chromatography apparatus enabling larger injection volumes and minimizing extra column effects acting upstream of a column, comprising:
   an analytical column having a stationary phase with a head;
   a focusing pre-column in fluid communication with said analytical column and placed upstream of said analytical column, wherein said focusing pre-column includes a stationary phase which separates solutes from the molecules of an injection solvent and enables focusing of solutes onto said head of said analytical column;
   wherein when used in a reversed phase mode said stationary phase of said focusing pre-column comprises particles of silica hydride to retain polar solutes in the presence of a non-polar solvent;
   wherein said stationary phase of said focusing pre-column comprises silica hydride particles with a generally polar phase bonded to said silica hydride particles, thereby enabling said focusing pre-column to retain non-polar solutes; and wherein said focusing pre-column has a narrower internal cross-sectional dimension than the internal cross-sectional dimension of said analytical column, such that the linear velocity on said focusing pre-column is higher than that on said analytical column, wherein the differential in linear velocity enables more efficient focusing of focuses the solutes at said head of said analytical column.

* * * * *